US012002153B2

(12) United States Patent
Shamir et al.

(10) Patent No.: US 12,002,153 B2
(45) Date of Patent: Jun. 4, 2024

(54) METHODS, SYSTEMS, AND APPARATUSES FOR MEDICAL IMAGE ENHANCEMENT TO OPTIMIZE TRANSDUCER ARRAY PLACEMENT

(71) Applicant: Novocure GmbH, Root (CH)

(72) Inventors: Reuven Ruby Shamir, Haifa (IL); Noa Urman, Haifa (IL); Yana Glozman, Haifa (IL)

(73) Assignee: Novocure GmbH, Root (CH)

( * ) Notice: Subject to any disclaimer, the term of this patent is extended or adjusted under 35 U.S.C. 154(b) by 40 days.

(21) Appl. No.: 17/578,241

(22) Filed: Jan. 18, 2022

(65) Prior Publication Data

US 2022/0237863 A1     Jul. 28, 2022

Related U.S. Application Data

(60) Provisional application No. 63/140,635, filed on Jan. 22, 2021.

(51) Int. Cl.
*G06T 17/00* (2006.01)
*A61B 5/055* (2006.01)
(Continued)

(52) U.S. Cl.
CPC .............. *G06T 17/00* (2013.01); *A61B 5/055* (2013.01); *A61B 34/10* (2016.02); *G06T 3/4053* (2013.01);
(Continued)

(58) Field of Classification Search
CPC ....... G06T 17/00; G06T 3/4053; A61B 5/055; A61B 34/10
(Continued)

(56) References Cited

U.S. PATENT DOCUMENTS 6,856,666 B2   2/2005   Lonn et al.
6,928,315 B1   8/2005   Nachaliel
(Continued)

FOREIGN PATENT DOCUMENTS

JP    2012000135 A   1/2012
JP    4965433 B2    4/2012

OTHER PUBLICATIONS

Noa Urman et al., "Investigating the Connection Between Tumor-Treating Fields Distribution in the Brain and Glioblastoma Patient Outcomes. A Simulation-Based Study Utilizing a Novel Model Creating Technique," Brain and Human Body Modeling, 2019, pp. 139-154.
(Continued)

*Primary Examiner* — Javid A Amini
(74) *Attorney, Agent, or Firm* — McCarter & English, LLP; Michael A. Sartori (57) ABSTRACT

A computer-implemented method to generate a three-dimensional model, wherein the computer comprises one or more processors and memory accessible by the one or more processors, and the memory stores instructions that when executed by the one or more processors cause the computer to perform the computer-implemented method, includes: receiving first image data of a first portion of the patient's body in a first image modality, receiving second image data of a second portion of the patient's body in a second image modality, modifying the second image data from the second image modality to the first image modality, and generating, based on the first image data in the first image modality and the modified second image data in the second image modality, a three-dimensional model of the first portion and the second portion of the patient's body.

19 Claims, 5 Drawing Sheets

(51) Int. Cl.
   *A61B 34/10* (2016.01)
   *G06T 3/40* (2006.01)
   *G06T 3/4053* (2024.01)
(52) U.S. Cl.
   CPC ..... *A61B 2034/105* (2016.02); *G06T 2210/41* (2013.01)
(58) Field of Classification Search
   USPC ........................................................ 345/419
   See application file for complete search history.

(56) References Cited

U.S. PATENT DOCUMENTS

| | | | |
|---|---|---|---|
| 7,565,205 B2* | 7/2009 | Palti | A61N 1/40 607/76 |
| 8,064,986 B2 | 11/2011 | Profio et al. | |
| 9,508,144 B2 | 11/2016 | Vilsmeier | |
| 9,639,938 B2 | 5/2017 | Blumhofer et al. | |
| 10,299,880 B2 | 5/2019 | Ramirez Luna et al. | |
| 10,966,798 B2 | 4/2021 | Tesar et al. | |
| 2006/0084867 A1* | 4/2006 | Tremblay | A61B 90/36 600/434 |
| 2007/0195923 A1* | 8/2007 | Netsch | G06T 11/005 378/4 |
| 2012/0150035 A1* | 6/2012 | Seip | A61N 7/02 600/439 |
| 2014/0080095 A1* | 3/2014 | Suttin | A61C 9/0053 433/202.1 |
| 2015/0279088 A1* | 10/2015 | Ma | A61B 8/4281 345/427 |
| 2017/0035517 A1* | 2/2017 | Geri | A61B 90/37 |
| 2020/0000552 A1* | 1/2020 | Mednikov | A61C 7/002 |
| 2020/0273560 A1* | 8/2020 | Wolf | G16H 70/20 |
| 2020/0375670 A1* | 12/2020 | Bonny | A61B 34/20 |
| 2022/0104822 A1 | 4/2022 | Shelton, IV et al. | |

OTHER PUBLICATIONS

Sebastian Bauer et al., "Real-Time Range Imaging in Health Care: A Survey," Time-of-Flight and Depth Imaging, 2013, pp. 228-254.

Mandar Kulkarni, "Depth Map Repairing Using Tensor Voting," 2012 International Conference on 3D Imaging (IC3D), IEEE, 2012, 6 pages.

Yadav et al., "Image fusion using hybrid methods in multimodality medical images," Medical & Biological Engineering & Computing, 22 pp., Jan. 2020.

Matthew J. Clarkson, "Registration of Optical images to 3D Medical Images," 263 pp., Jun. 2000.

Aguilar et al., "Fusion of Multi-Modality Volumetric Medical Imagery," Proc. of the Fifth International Coference on Information Fusion, 7 pp., 2002.

* cited by examiner

METHODS, SYSTEMS, AND APPARATUSES FOR MEDICAL IMAGE ENHANCEMENT TO OPTIMIZE TRANSDUCER ARRAY PLACEMENT

CROSS-REFERENCE TO RELATED APPLICATIONS

This application claims priority to U.S. Provisional Application No. 63/140,635, filed Jan. 22, 2021, which is hereby incorporated by reference in its entirety.

BACKGROUND

Tumor Treating Fields (TTFields) are low intensity alternating electric fields within the intermediate frequency range, which may be used to treat tumors as described in U.S. Pat. No. 7,565,205. TTFields are induced non-invasively into the region of interest by transducers placed on the patient's body and applying AC voltages between the transducers. To determine effective positioning of the transducers on the patient's body, a three-dimensional model of a portion of the patient's body may be evaluated. However, sufficient image data for the patient may not be available to generate the three-dimensional model because the available image data for the patient may be missing a portion of the body, because a resolution of the image data may be insufficient to generate the three-dimensional model, or because image data for a first portion of the body is of a different image modality from image data for a second portion of the body. As such, any of these problems can prevent the generation of a three-dimensional model of the portion of the patient's body and thereby prevent effective positioning of transducers on the patient's body to induce TTFields.

SUMMARY

One aspect of the invention is directed to a computer-implemented method to generate a three-dimensional model, the computer comprising one or more processors and memory accessible by the one or more processors, the memory storing instructions that when executed by the one or more processors cause the computer to perform the method, the method including: receiving first image data of a first portion of the patient's body in a first image modality; receiving second image data of a second portion of the patient's body in a second image modality; modifying the second image data from the second image modality to the first image modality; and generating, based on the first image data in the first image modality and the modified second image data in the second image modality, a three-dimensional model of the first portion and the second portion of the patient's body.

The above aspect of the invention is exemplary, and other aspects and variations of the invention will be apparent from the following detailed description of embodiments.

DETAILED DESCRIPTION

As discovered by the inventors, the disclosed subject matter provides methods and systems for generating a three-dimensional model of a portion of a patient's body given an incomplete or inconsistent image set. The three-dimensional model can then be used to determine locations to place transducers on the patient's body to generate TTFields.

The incomplete or inconsistent image set of the patient's body may be, for example: an image set missing a portion of the patient's body; an image set with a resolution insufficient to generate the three-dimensional model; or an image set for a first portion of the patient's body having a different image modality from image data for a second portion of the patient's body. Using one or more of the inventive techniques, a three-dimensional model of a portion of the patient's body may then be generated given such an incomplete or inconsistent image set.

Figure 1:
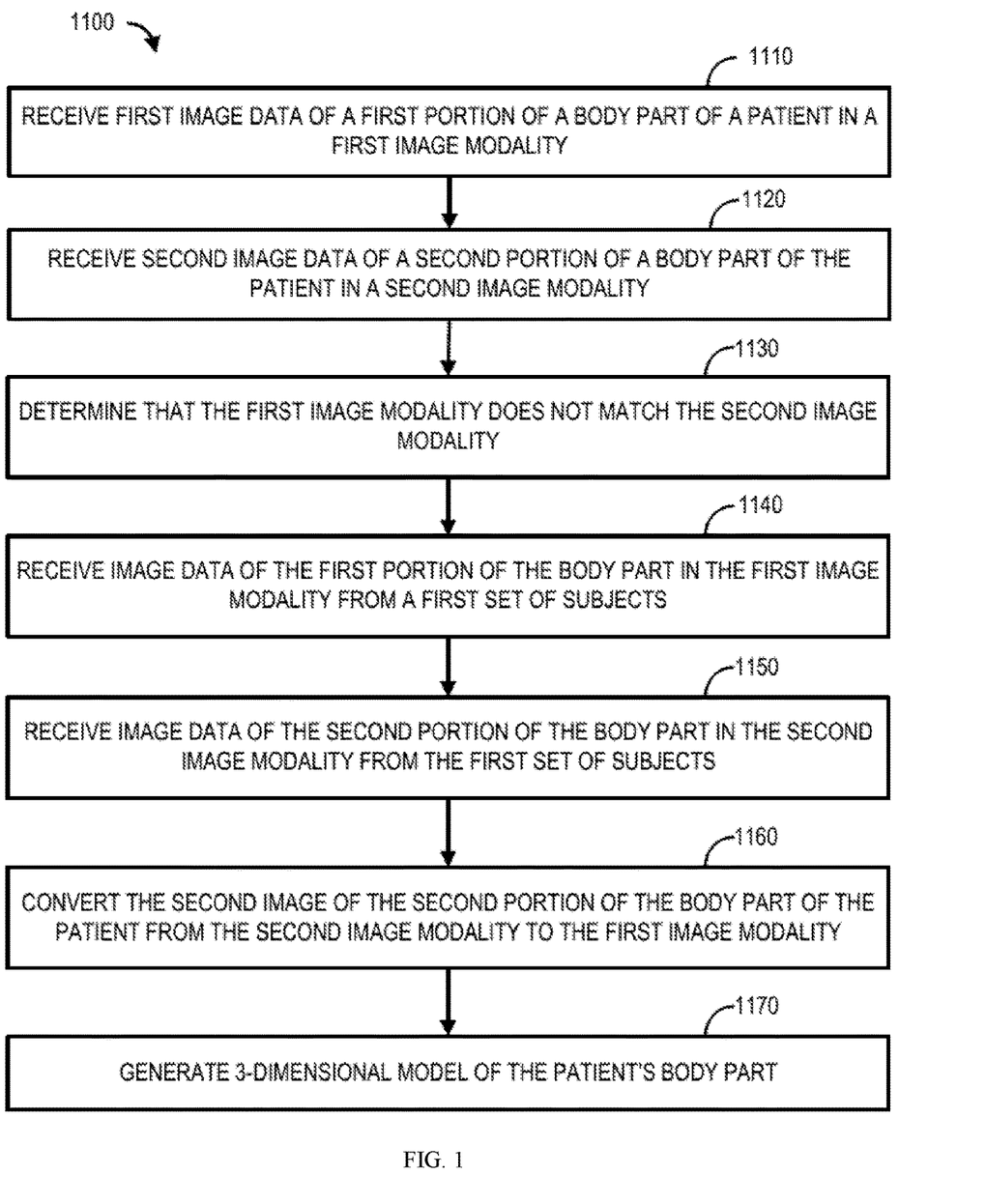
FIG. 1 is a flowchart of an example method for generating a three-dimensional image of a patient's body part based on two image scans of the patient.

FIG. 1 is a flowchart of an example method 1100 for generating a three-dimensional image of a patient's body part based on two image scans of the patient, wherein at least a portion of the two image scans comprise different portions of the patient's body part and wherein the two image scans have different image modalities. The two images of the patient, in different image modalities, may each be images of the same patient body part. The method described herein may be implemented for any body part of the patient.

At 1110, a patient support system 1002 may receive first image data of a first portion of a patient's body part in a first image modality. For example, the first portion of the patient's body part may be a first portion of the patient's head. In addition, the first image data may not include at least a portion of a second portion of the patient's head. For example, the first image data may include a lower portion of the patient's head (e.g., or other body part), but may not include at least a portion of the upper portion of the patient's head (e.g., or other body part).

At 1120, the patient support system 1002 may receive second image data of a second portion of a patient's body in a second image modality different from the first image modality. For example, the second portion of the patient's body part may be a second portion of the patient's head. In addition, the second image data may not include at least a portion of the first portion of the patient's head. For example, the second image data may include an upper portion of the patient's head (e.g., or other body part), but may not include at least a portion of the lower portion of the patient's head (e.g., or other body part).

The image modality for the received first/second image data may be x-ray computer tomography (CT) data and the second image data may be x-ray CT data. In another example, the first/second image modality may be any one of single photon emission computed tomography (SPECT) data, magnetic resonance imaging (MRI) data, positron emission tomography (PET) data, or the like, and the second image may comprise SPECT data, MRI data, PET data, or the like. The first/second image data may be received by a predictive modeling application 1014 from imaging data 610, a local database 1018, or a remote image database 1020. The first image data and the second image data may be taken at the same or different orientation of the patient's body part. The first image data and the second image data of the portion of the body of the patient may have been taken at the same or different times.

At 1130, the patient support system 1002 may determine that the first image modality for the first image data does not match the second image modality for the second image data. The predictive modeling application 1014 may compare the modality fields for the files of each of the first image scan and second image scan to determine if the modality for each of the first image scan and the second image scan is the same or different. The modality field may provide an indicator that indicates the modality of the image scans. If the predictive modeling application 1014 compares the information in the modality field for each modality of the first image scan and the second image scan and determines they are the same, the predictive modeling application 1014 may use the first image scan and the second image scan to generate a full three-dimensional image of the body part of the patient substantially as described at 1170. In this example, the predictive modeling application 1014 compares the information in the modality field for each image modality of the first image scan and the second image scan and determines that the modalities are different.

The predictive modeling application 1014 may have access to a plurality of images of body parts for other subjects. This plurality of images may include a first portion of images comprising image data of the first portion of the body part in the first modality for subjects and a second portion of images comprising image data of the second portion of the body part in the second image modality for the subjects. This plurality of images may be stored in the image database 1018 of the patient support system 1002 and/or may be accessed from another image database 1020, which may be remote from the patient support system 1002.

The predictive modeling application 1014 may query the database 1018, 1020 to retrieve a plurality of images for developing a model to convert an image from one image modality to another image modality. The query may determine, for example, for subjects other than the patient, which images in the database are of the same subject and include image data of the first portion of the body part of the subject in the first image modality and separate image data for the second portion of the body part of the subject in the second image modality. Groups of image data that satisfy this query may be selected for analysis in creation of the modality translation model.

The number of subject images used for the creation of the modality translation model may be configurable and can be any number greater than image data for one subject other than the patient. In certain example embodiments, a target or threshold number of subjects which satisfy the query criteria must be satisfied in order to create the modality translation model. In certain example embodiments, the target threshold may be image data for at least 5 subjects that satisfy the query. For example, the target threshold may be in the range of image data for 15-50 subjects that satisfy the query.

In certain example embodiments, the predictive modeling application 1014 may only collect image data for the first portion of the body part in the first image modality and image data for the second portion of the body part in the second image modality for the number of subjects that equal the target threshold. In other example embodiments, the predictive modeling application may collect image data for the first portion of the body part in the first image modality and image data for the second portion of the body part in the second image modality for any number of subjects that satisfies the target threshold and that is available in the image database.

The query of the database 1018, 1020 may also include one or more other query optimization factors. For example, at least a portion of these factors may be based on one or more physical attributes of the patient/subject. For example, the query optimization factors may include one or more of the age of the patient, an age range, the height of the patient, a height range, the sex of the patient, the race of the patient, the weight of the patient, a weight range, one or more diseases, conditions, or abnormalities of the patient, one or more dimensions of the body part, a ratio of one or more dimensions of the body part, or the like. In certain example embodiments, multiple super resolution models may be generated based on one or more of these query optimization factors. The determination of the number and/or type of factors to include in the query can be configurable and/or determined by a user.

At 1140, the predictive modeling application 1014 may receive a first plurality of image data of at least the first portion of the body part for a number of other subjects. The images of the at least the first portion of the body part for these other subjects may be in the first image modality (e.g., MRI). The images of at least the first portion of the body part may be received based on a query of the database 1018, 1020. The query of the database may or may have not included one or more query optimization factors.

At 1150, the predictive modeling application 1014 (e.g., or another portion of the patient support system 1002) may receive a second plurality of image data of at least the second portion of the body part for the number of subjects for which the first image data was received. The image data of at least the second portion of the body part for these subjects may be in the second image modality (e.g., x-ray CT). The images of the second portion of the body part may be received based on the query of the database 1018, 1020. The query of the database may or may have not included one or more query optimization factors.

At 1160, the predictive modeling application 1014 may convert the second image scan of the second portion of the body part of the patient from the second image modality to the first image modality. For example, the predictive modeling application 1014 may employ artificial intelligence techniques to use the first plurality of image data of at least the first portion of the body part of the other subjects in the first image modality and the second plurality of image data of at least the second portion of the body part of the other subjects in the second image modality to generate an image modality translation model for converting image data in the second image modality to image data in the first image modality.

For example, the predictive modeling application 1014, may apply a form of Generative Adversarial Network (GAN) analysis to generate the image modality translation model. For example, the predictive modeling application 1014 may apply a MedGAN analysis to generate the image modality translation model. In other examples, the predictive modeling application 1014 may apply another form of GAN analysis including, but not limited to, Super Resolution GAN, pix2pix GAN, CycleGAN, DiscoGAN, and FilasGAN. In other example embodiments, the predictive modeling application 1014 may apply another form of modeling to generate the image modality translation model, such as Projective Adversarial Network (PAN) or Variational Auto-encoders (VAE).

Once the image modality translation model has been generated based on the first plurality of image data of at least the first portion of the body part of the other subjects in the first image modality and the second plurality of image data of at least the second portion of the body part of the other subjects in the second image modality, the predictive modeling application 1014 may apply the model to the image scan for the second portion of the body part of the patient in the second image modality to convert the second image scan from the second image modality (e.g., x-ray CT) to the first image modality (e.g., MRI) and/or the same image modality as the first image scan of the first portion of the body part of the patient.

At 1170, the predictive modeling application 1014 may generate a complete three-dimensional model of the body part of the patient based on the first image data of the first portion of the body part of the patient in the first image modality and the converted second image data of the second portion of the body part of the patient body in the first image modality. For example, as the first image and the converted second image for the patient are in the same image modality, the predictive modeling application 1014 may overlay or otherwise combine all or a portion of the converted second image data of the second portion of the body part of the patient over the first image data of the first portion of the body part of the patient and may add to the first image data the portion of the patient's body part that is in the converted second image data but not in the first image data. For example, the body part may be the patient's head. The first image may comprise a portion of the patient's head, but may also be missing another portion of the patient's head (e.g., at least a portion of the upper portion of the patient's head). The converted second image data may include the portion of the desired body part that is missing from the first image data. For example, the converted second image data may include the upper portion of the patient's head but also may not include all of the patient's head. The predictive modeling application 1014 may generate a complete three-dimensional model of the patient's head by taking the image data of the converted second image for the portion of the body part missing in the first image data and adding that image data to the first image data to create a digital representation in three-dimensional space of all or a portion of the body part of the patient, including internal structures, such as tissues, organs, tumors, etc.

Figure 2:
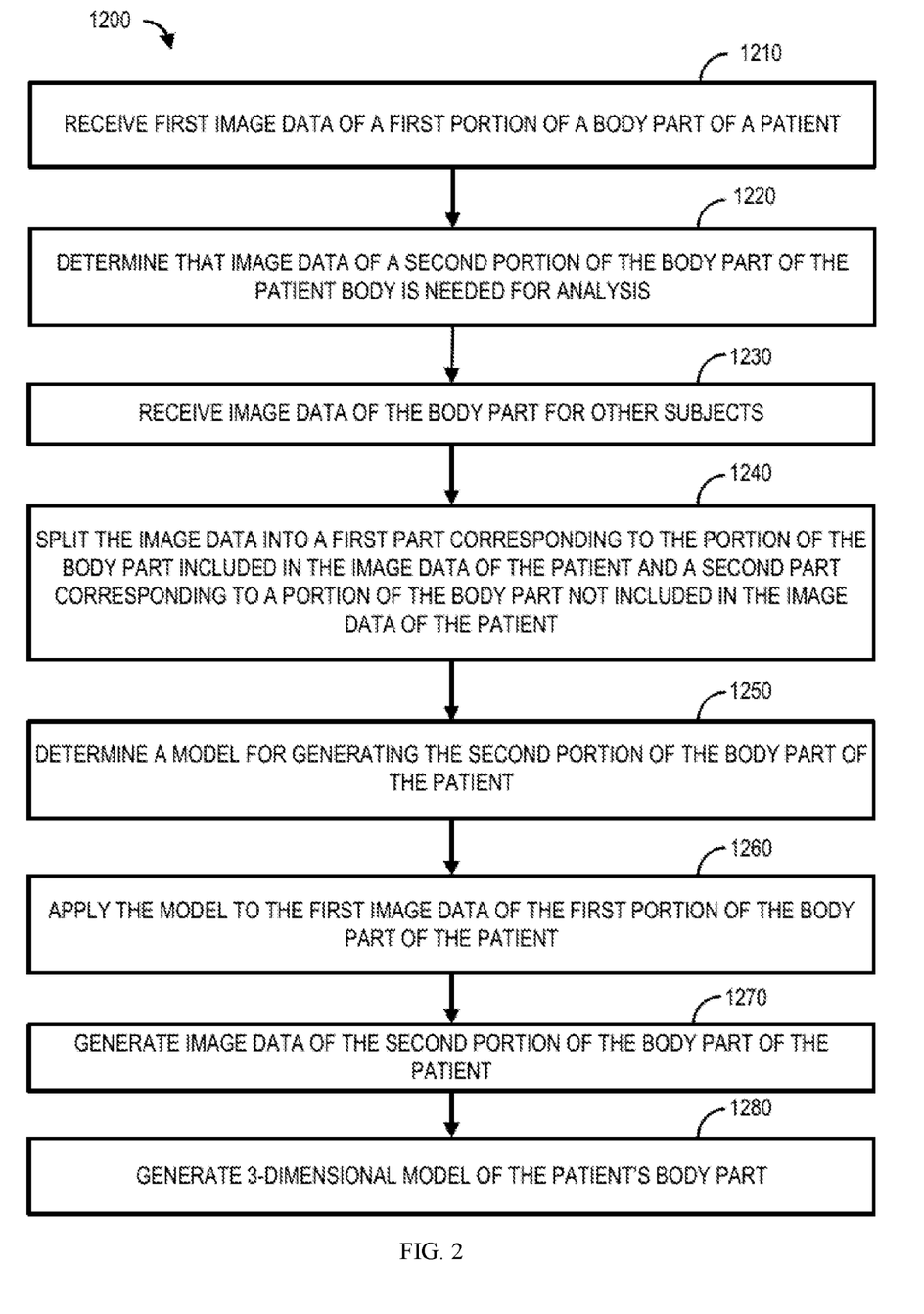
FIG. 2 is a flowchart of an example method for generating a three-dimensional image of a patient's body part based on a single image scan of the patient.

FIG. 2 is a flowchart of an example method 1200 for generating a three-dimensional image of a patient's body part based on a single image scan comprising a portion of the body part of the patient and wherein the image data does not include another portion of the body part of the patient.

At 1210, the patient support system 1002 may receive first image data of a first portion of a patient's body part. The first image may not include at least a portion of a second portion of the body part of the patient.

At 1220, the patient support system 1002 may determine that a second portion of the body part of the patient is needed to generate a complete three-dimensional model of the body part. For example, the patient support system 1002 may evaluate the first image data and determine that the image data only include a portion of the body part needed for modeling the delivery of the TTFields to the body part of the patient.

At 1230, the predictive modeling application 1014 may query a database for image data of the body part of one or more subjects that is the same as the body part of the patient. In response to the query, the predictive modeling application 1014 may receive a plurality of image data of the body part for a plurality of subjects other than the patient. The predictive modeling application 1014 may query the database 1018, 1020 to retrieve a plurality of images for developing a body part completion model to add image data representing additional portions of the body part to the first image data of the body part of the patient. For example, adding image data representing additional portions of the body part of the first image data of the body part may result in a complete or more complete image of the body part of the patient. The query may determine, for example, for subjects other than the patient, which images in the database are of the same body part of the subject as that of the patient. The query may narrow to include image data for images of the same body part of the subject as that of the patient, wherein the image data of the subject represents a complete or more complete image of the body part than the first image data for the patient. Image data that satisfies this query may be selected for analysis in creation of a body part completion model.

At 1240, the predictive modeling application 1014 may split the received image data for each subject into at least two parts. For example, the predictive modeling application 1014 may split the received image data for the body part of each subject into a first part that comprises a first portion of the body part and a second part that comprises a second portion of the body part. For example, the first part may be the portion of the body part that is usually included in a clinical scan. For the example head, the first part may be most of the head other than a top portion of the head and/or one or more side portions of the head for each subject. For example, the second part may be a portion of the body part that is usually not included in a clinical scan.

At 1250, the predictive modeling application 1014 may determine a body part completion model for generating a remainder of all or a portion of the body part from the image data. The predictive modeling application 1014 may employ artificial intelligence techniques and the first and second parts of the image data of the body part of the plurality of subjects to determine the body part completion model for generating a remainder of all or a portion of the body part from the image data of the body part of the patient. In one example, the predictive modeling application 1014 may employ statistical shape analysis of the first part and second part of the image data for the body part of the plurality of subjects to determine the body part completion model. In another example, the predictive modeling application 1014 may employ active appearance modeling of the first part and second part of the image data for the body part of the plurality of subjects to determine the body part completion model. In another example, the predictive modeling application 1014 may employ global image statistics of the first part and second part of the image data for the body part of the plurality of subjects to determine the body part completion model. Any one of the proposed techniques used to determine a body part completion model may model the head image statistics and the geometrical relations between the head and/or brain structures in the segments first parts and second parts of the image data for the body part of the plurality of subjects. After training on the large datasets, machine learning regressors (e.g., random forest) can be incorporated to predict the missing part of the body part from the first image data. In another example, the predictive modeling application 1014 may employ GAN analysis, (e.g., MedGAN, Super Resolution GAN, pix2pix GAN, CycleGAN, DiscoGAN, and Fila-sGAN) to increase the dataset being evaluated to include a large number (e.g., more than 100, more than 1000, more than 5000) of simulated image scans of the body part. The first part and second part of the image data for the body part of the plurality of subjects may then be entered as input into an artificial neural network that contains some convolutional blocks in it and will be trained to output an image of the whole body part (e.g., the whole head, torso, arm, leg, etc.) the includes the missing portion of the body part within the determined body part completion model.

At 1260, the predictive modeling application 1014 may apply the body part completion model to the first image scan of the first portion of the body part of the patient. For example, the body part completion model may be applied by way of artificial intelligence techniques to the image data of the first portion of the body part of the patient to determine all or at least a portion of the remaining portion of the body part of the patient not included in the first image scan of the body part.

At 1270, the predictive modeling application 1014 may generate second image data for a second portion of the body part of the patient that complements and is based on the image data of the first portion of the body part of the patient. The image data for the second portion of the body part may be a three-dimensional discreet image representing the second portion of the body part of the patient. In one example, the second image data representing the second portion of the body part of the patient may be any remaining portion of the body part that is not included in the first image data.

At 1280, the predictive modeling application 1014 may generate a complete three-dimensional model of the body part (or a portion of the body part) of the patient based on the first image data of the first portion of the body part of the patient and the generated second image data of the second portion of the body part for the patient.

Figure 3:
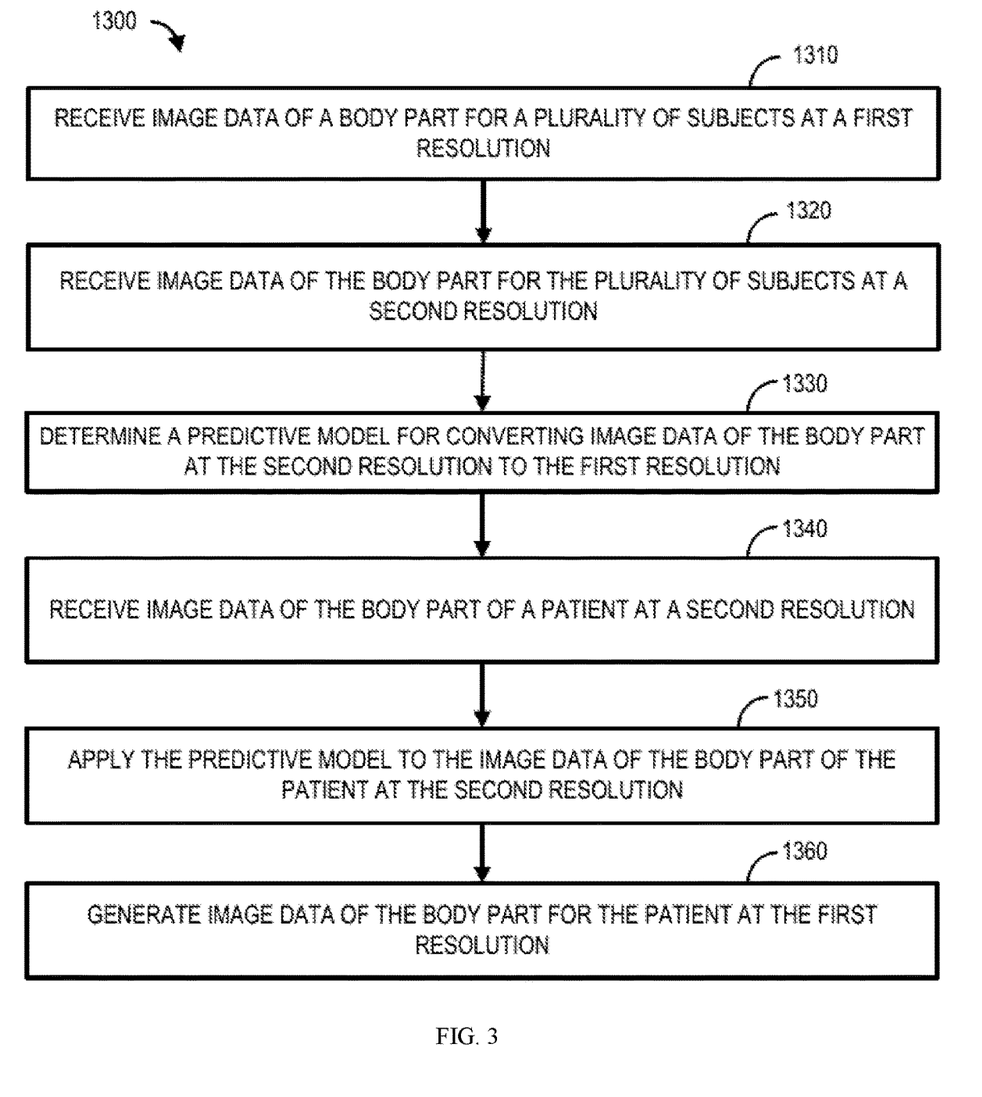
FIG. 3 is a flowchart of an example method for generating a high resolution three-dimensional image of a patient's body part based on a low resolution image of the patient's body part.

FIG. 3 is a flowchart of an example method 1300 for generating a high resolution three-dimensional image (e.g., MRI) of a patient's body part based on a low resolution image (e.g., SPECT scan or PET scan) of the patient's body part. The image data of the low resolution image scan may be that of an entire body part or a portion of the body part of the patient.

At 1310, a predictive modeling application 1014 may receive a plurality of first image data of the body part for a number of other subjects at a first resolution. The first resolution may be a high resolution (e.g., an MRI or x-ray CT image). Each of the first image data may be of the same image modality. The plurality of first image data may be received based on a query of the database 1018, 1020. The query may or may not include the optimization factors.

The predictive modeling application 1014 may query the database 1018, 1020 to retrieve a plurality of images for developing a model to generate high-resolution image data (e.g., MRI) based on low-resolution image data (e.g., SPECT scan or PET scan) of a body part of the patient. The query may determine, for example, for subjects other than the patient, which images in the database are of the same subject and include image data of the body part of the subject in the both high resolution and low resolution. Groups of image data that satisfy this query may be selected for analysis in the creation of the super resolution model. The number of subject images used for the creation of the super resolution model may be configurable and can be any number greater than one subject other than the patient. In certain example embodiments, a target or threshold number of subjects which satisfy the query criteria must be satisfied in order to create the super resolution model. In certain example embodiments, the target threshold may be image data for at least 100 subjects that satisfy the query (e.g., low-resolution image data and high-resolution image data for the body part). For example, the target threshold may be in the range of image data for 50-5000 subjects that satisfy the query. In certain example embodiments, the predictive modeling application 1014 may only collect low-resolution image data and high resolution image data for the body part for the number of subjects that equal the target threshold. In other example embodiments, the predictive modeling application 1014 may collect low-resolution image data and high resolution image data for the body part for any number of subjects that satisfies the target threshold and that is available in the image database 1018, 1020.

At 1320, the predictive modeling application 1014 may receive a plurality of second image data of the body part for the plurality of subjects. Accordingly, for each subject, the predictive modeling application 1014 may receive both first image data and second image data of the body part. Each of the plurality of second image data may be at a second resolution. The second resolution may be a low resolution. Each of the plurality of second image data may be of the same image modality and may be different from the image modality of the first image data. The plurality of second image data may be received based on a query of the database 1018, 1020. The query may or may have not included optimization factors.

At 1330, the predictive modeling application may determine a super resolution model for generating image data of a body part of a patient in high resolution (e.g., MRI) based on image data of the body part of the patient in low resolution (e.g., SPECT data or PET data). For example, the predictive modeling application 1014 may employ artificial intelligence techniques to use the plurality of first image data of a body part for a plurality of subjects and the plurality of second image data of the body part for the plurality of subjects to generate a super resolution model for generating high-resolution image data of the body part for the patient based on low-resolution image data of the body part for the patient. For example, the predictive modeling application 1014 may apply a form of Generative Adversarial Network (GAN) analysis on the plurality of first image data and the plurality of second image data of the body part for the plurality of subjects to generate the super resolution model. For example, the predictive modeling application 1014 may apply a MedGAN analysis to generate the super resolution model. In other examples, the predictive modeling application 1014 may apply another form of GAN analysis including, but not limited to, Super Resolution GAN, pix2pix GAN, CycleGAN, DiscoGAN, and Fila-sGAN. The predictive modeling application 1014 may apply another form of modeling to generate the super resolution model (e.g., such as regression models or convolutional networks).

At 1340, the predictive modeling application 1014 may receive image data of a body part for a patient. The image data of the body part may be at a second resolution that is a low resolution (e.g., lower than the resolution of MRI image data).

At 1350, once the super resolution model has been generated based on the plurality of first image data of a body part at a first resolution and the plurality of second image data of the body part at a second resolution for the plurality of subjects (e.g., persons), the predictive modeling application 1014 may apply the model to the received image data of the body part for the patient at the second resolution. In certain examples, the super resolution model may be generated prior to receipt of the image data of the body part for the patient. In other example embodiments, the super resolution model may be generated after receipt of the image data of the body part for the patient.

At 1360, the predictive modeling application 1014 may generate image data of the body part for the patient at a first resolution. The generation of the image data of the body part for the patient at the first resolution may be based on applying the super resolution model to the received image data of the body part for the patient at the second resolution. The first resolution may be higher than the second resolution. The generated image data of the body part for the patient at the first resolution may be a complete three-dimensional model of the body part of the patient based on the image data of the body part of the patient at the second resolution and the super resolution model.

Figure 4:
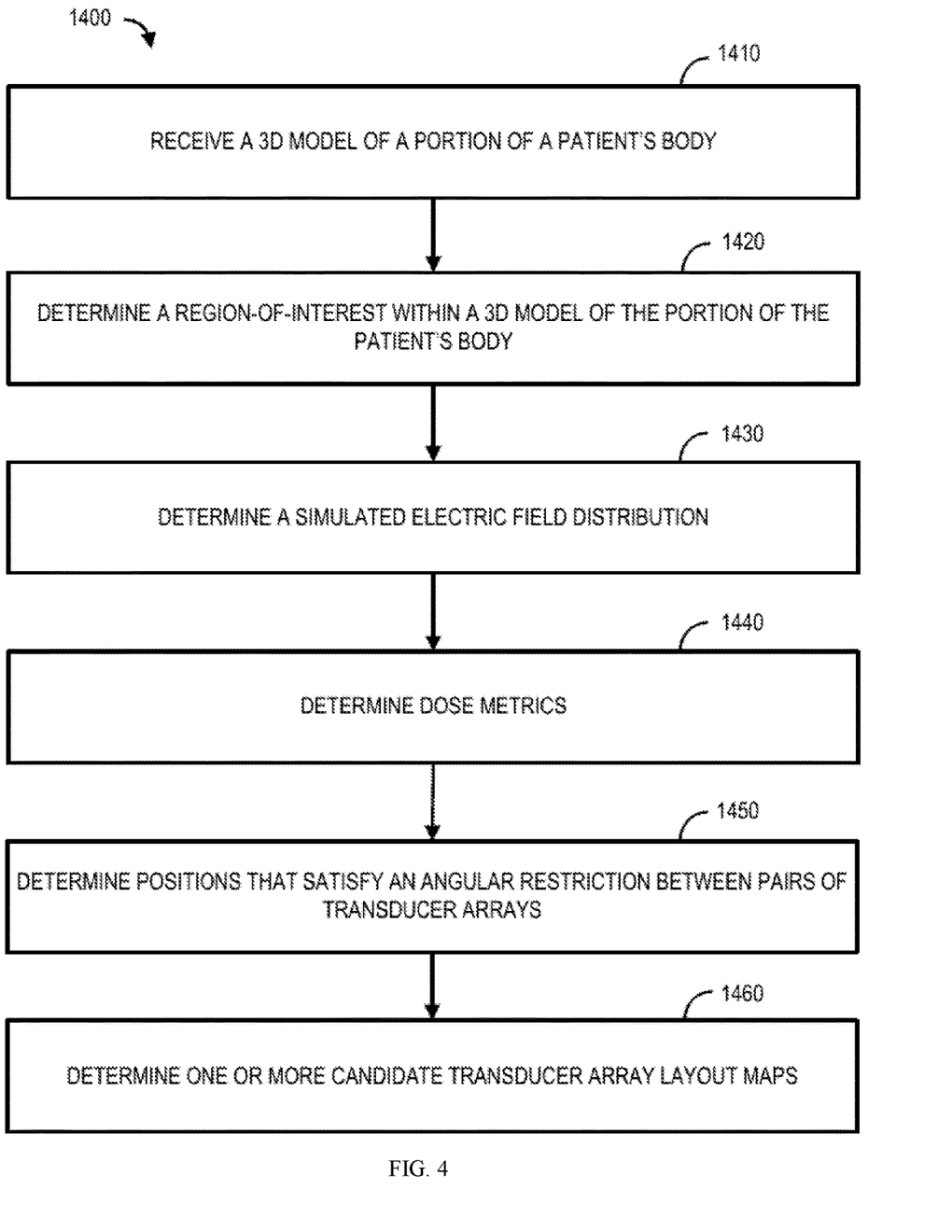
FIG. 4 is a flowchart for an example method for determining transducer array layout for the delivery of TTFields to a portion of a patient's body.

FIG. 4 is a flowchart for an example method 1400 for determining transducer array layout for the delivery of TTFields to a portion of a patient's body. The method 1400 may be completed by one or more of the apparatus 100, the patient support system 1002, a patient modeling application 608, and/or any other device/component described herein.

At 1410, a three-dimensional model of a portion of a patient's body may be received. For example, the three-dimensional model may be received by the patient modeling application 608. The three-dimensional (3D) model may be a 3D model generated in one or more of FIGS. 1-3 and may comprise a body part or a portion of a body part of a patient. At 1420, a region-of-interest (ROI) may be determined within the 3D model of a portion of a patient's body. At 1430, a simulated electric field distribution may be determined. At 1440, dose metrics may be determined. For example, the dose metrics may be determined based on the simulated electric field distributions. For example, a dose metric may be determined for each pair of positions of the plurality of pairs of positions for the transducer arrays. At 1450, one or more sets of pairs of positions of the plurality of pairs of positions that satisfy an angular restriction between pairs of transducer arrays are determined. For example, the angular restriction may be and/or indicate an orthogonal angle between the plurality of pairs of transducer arrays. The angular restriction, for example, may be and/or indicate a range of an angle between the plurality of pairs of transducer arrays. At 1460, one or more candidate transducer array layout maps may be determined. For example, the one or more candidate transducer array layout maps may be determined based on the dose metrics and the one or more sets of pairs of positions that satisfy the angular restriction. In some instances, the method 1400 may comprise adjusting a simulated orientation or a simulated position for at least one transducer array at at least one position of the one or more candidate transducer array layout maps, and determining, based on adjusting the simulated orientation or the simulated position for the at least one transducer array, a final transducer array layout map.

Figure 5:
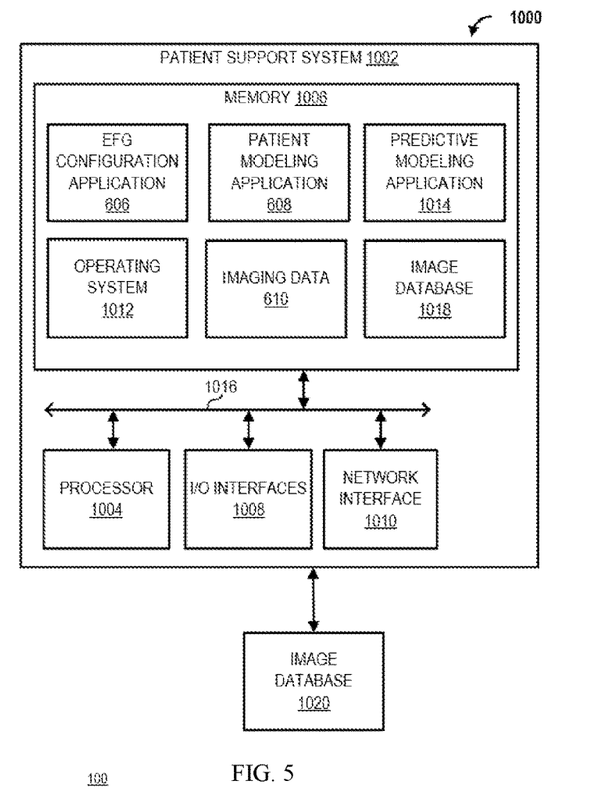
FIG. 5 is a block diagram depicting an example operating environment.

FIG. 5 is a block diagram depicting an environment 1000 comprising a non-limiting example of a patient support system 1002. In an aspect, some or all steps of any described method may be performed on a computing device as described herein. The patient support system 1002 can comprise one or multiple computers configured to store one or more of the electric field generator (EFG) configuration application 606, the patient modeling application 608, the imaging data 610, operating system (O/S) 1012, the predictive modeling application 1014, the image database 1018, and the like.

The patient support system 1002 can be a digital computer that, in terms of hardware architecture, generally includes one or more processors 1004, a memory system 1006, input/output (I/O) interfaces 1008, and network interfaces 1010. These components (1004, 1006, 1008, and 1010) are communicatively coupled via a local interface 1016. The processor 1004 can be a hardware device for executing software, particularly for software stored in memory system 1006. When the patient support system 1002 is in operation, the processor 1004 can be configured to execute software stored within the memory system 1006, to communicate data to and from the memory system 1006, and to generally control operations of the patient support system 1002 pursuant to the software. The patient support system 1002 may be a computer that includes one or more processors and memory accessible by the one or more processors, where the memory stores instructions that when executed by the one or more processors cause the computer to perform one or more of the methods disclosed herein.

The patient modeling application 608 may be configured to generate a 3D model of a portion of a body of a patient according to the imaging data 610. The imaging data 610 may comprise any type of visual data, for example, single-photon emission computed tomography (SPECT) image data, x-ray computed tomography (CT) data, magnetic resonance imaging (MRI) data, positron emission tomography (PET) data, and data that can be captured by an optical instrument. In certain implementations, image data may include 3D data obtained from or generated by a 3D scanner. The patient modeling application 608 may also be configured to generate a 3D array layout map based on the patient model and one or more electric field simulations. To properly optimize array placement on a portion of a patient's body, the imaging data 610, such as MRI imaging data, may be analyzed by the patient modeling application 608 to identify a region of interest that comprises a tumor. In an aspect, the patient modeling application 608 may be configured to determine a desired transducer array layout for a patient based on the location and extent of the tumor. In an aspect, the patient modeling application 608 can be configured to determine the 3D array layout map for a patient.

The network interface 1010 can be used to transmit and receive from the patient support system 1002. In the example of FIG. 5, the software in the memory system 1006 of the patient support system 1002 can comprise the EFG configuration application 606, the patient modeling application 608, the imaging data 610, the predictive modeling application 1014, the image database 1018, and the operating system 1012.

The predictive modeling application 1014 can be one or more modeling applications for generating image data models based on image data from a plurality of subjects. The predictive modeling application may be configured to conduct any one or more of Generative Adversarial Network (GAN) analysis, MedGAN analysis, Super Resolution GAN, pix2pix GAN, CycleGAN, DiscoGAN, Fila-sGAN, Projective Adversarial Network (PAN) analysis, Variational Autoencoders (VAE), analysis, regression analysis, or convolutional network analysis. For example, the predictive modeling application 1014 may employ one or more artificial intelligence techniques to conduct the analysis of the subject image data.

Figure 6:
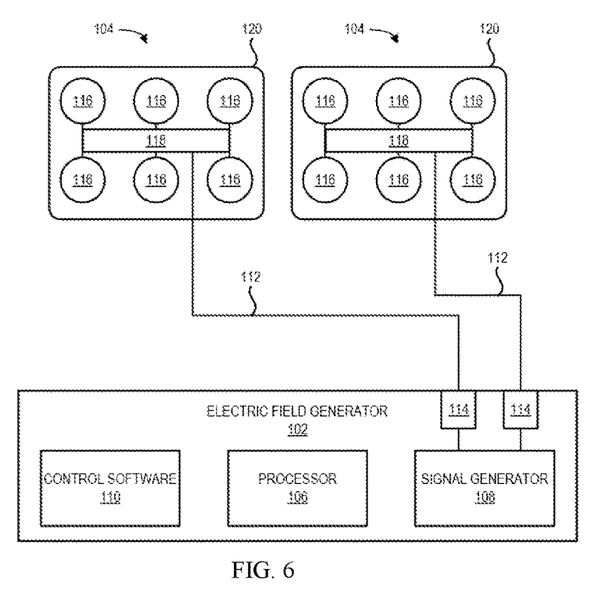
FIG. 6 shows an example apparatus for electrotherapeutic treatment.

FIG. 6 shows an example apparatus 100 for electrotherapeutic treatment. The apparatus 100 may comprise an electric field generator 102 and one or more transducer arrays 104. The apparatus 100 may be configured to generate TTFields via the electric field generator 102 and deliver the TTFields to an area of the body through the one or more transducer arrays 104. The electric field generator 102 may comprise one or more processors 106 in communication with a signal generator 108. The electric field generator 102 may comprise a control software 110 configured to control the performance of the processor 106 and the signal generator 108. The control software 110 may be stored in memory accessible by the one or more processors 106. The signal generator 108 may generate one or more electric signals in the shape of waveforms or trains of pulses. The signal generator 108 may be configured to generate an alternating voltage waveform at frequencies in the range, for example, from approximately 50 kHz to approximately 500 kHz. The voltages are such that the electric field intensity in tissue to be treated may be in the range of, for example, approximately 0.1 V/cm to approximately 10 V/cm.

One or more outputs 114 of the electric field generator 102 may be coupled to one or more conductive leads 112 that are attached at one end thereof to the signal generator 108. The opposite ends of the conductive leads 112 are connected to the one or more transducer arrays 104 that are activated by the electric signals. Output parameters of the signal generator 108 may comprise an intensity of the field, a frequency of the waves, and a maximum allowable temperature of the one or more transducer arrays 104. The output parameters may be set and/or determined by the control software 110 in conjunction with the processor 106.

The one or more transducer arrays 104 arrays may comprise one or more electrodes 116. The electrodes 116 may be biocompatible and coupled to a flexible circuit board 118. The electrodes 116, hydrogel, and the flexible circuit board 118 may be attached to a hypoallergenic medical adhesive bandage 120 to keep the one or more transducer arrays 104 in place on the body and in continuous direct contact with the skin. Each transducer array 104 may comprise one or more sensors, such as thermistors to measure skin temperature beneath the transducer arrays 104. The one or more transducer arrays 104 may vary in size and may comprise varying numbers of electrodes 116. A transducer array 104 may be configured for placement on a particular part of a patient's body, such as the head, the torso, the arm, or the leg of the patient.

In one example, the electrodes 116 may be ceramic disks, and each of the ceramic disks may be approximately 2 cm in diameter and approximately 1 mm in thickness. In another example, the electrodes 116 may be ceramic elements that are not disk-shaped. In yet another example, the electrodes 116 may be non-ceramic dielectric materials positioned over a plurality of flat conductors. Examples of non-ceramic dielectric materials positioned over flat conductors may include polymer films disposed over pads on a printed circuit board or over flat pieces of metal. In particular embodiments, transducers that use an array of electrodes that are not capacitively coupled may also be used. In this situation, each electrode element 116 may be implemented using a region of a conductive material that is configured for placement against a subject's body, with no insulating dielectric layer disposed between the conductive elements and the body. In other embodiments, the transducer may include only a single electrode element. As an example, the single electrode element may be a flexible organic material or flexible organic composite positioned on a substrate. As another example, the transducer may include a flexible organic material or flexible organic composite without a substrate.

Other alternative constructions for implementing a transducer for use with embodiments of the invention may also be used, as long as they are capable of (a) delivering TTFields to the subject's body and (b) being positioned at the locations specified herein.

The invention includes other illustrative embodiments, such as the following.

Illustrative Embodiment 1: A non-transitory computer-readable medium comprising instructions to generate a three-dimensional model, the instructions when executed by a computer cause the computer to perform a method comprising: receiving first image data of a first portion of the patient's body in a first image modality, receiving second image data of a second portion of the patient's body in a second image modality, modifying the second image data from the second image modality to the first image modality, and generating, based on the first image data in the first image modality and the modified second image data in the second image modality, a three-dimensional model of the first portion and the second portion of the patient's body.

Illustrative Embodiment 2: A non-transitory computer-readable medium comprising instructions to generate a three-dimensional model, the instructions when executed by a computer cause the computer to perform a method comprising: receiving first image data of a first portion of a body part of a patient, wherein the first portion of the body part is less than a complete body part, receiving a plurality of second image data of the body part for a plurality of subjects, determining, based on the plurality of second image data, a body part completion model, generating, based on the body part completion model and the first image data, third image data of a second portion of the body part, and generating, based on the first image data and the third image data, a three-dimensional model of the body part of the patient.

Illustrative Embodiment 3: A non-transitory computer-readable medium comprising instructions to generate a three-dimensional model, the instructions when executed by a computer cause the computer to perform a method comprising: receiving first image data of a portion of a patient's body at a first image resolution, receiving a plurality of second image data for a plurality of subjects, determining, based on the plurality of second image data, a super resolution model for increasing a resolution of the first image data, and generating, based on the super resolution model and the first image data, third image data of the portion of the patient's body at a second image resolution, wherein the second image resolution is greater than the first image resolution.

Illustrative Embodiment 4: A system to generate a three-dimensional model, the system comprising one or more processors and memory accessible by the one or more processors, the memory storing instructions that when executed by the one or more processors cause the system to perform a method comprising: receiving first image data of a first portion of the patient's body in a first image modality, receiving second image data of a second portion of the patient's body in a second image modality, modifying the second image data from the second image modality to the first image modality, and generating, based on the first image data in the first image modality and the modified second image data in the second image modality, a three-dimensional model of the first portion and the second portion of the patient's body.

Illustrative Embodiment 5: A system to generate a three-dimensional model, the system comprising one or more processors and memory accessible by the one or more processors, the memory storing instructions that when executed by the one or more processors cause the system to perform a method comprising: receiving first image data of a first portion of a body part of a patient, wherein the first portion of the body part is less than a complete body part, receiving a plurality of second image data of the body part for a plurality of subjects, determining, based on the plurality of second image data, a body part completion model, generating, based on the body part completion model and the first image data, third image data of a second portion of the body part, and generating, based on the first image data and the third image data, a three-dimensional model of the body part of the patient.

Illustrative Embodiment 6: A system to generate a three-dimensional model, the system comprising one or more processors and memory accessible by the one or more processors, the memory storing instructions that when executed by the one or more processors cause the system to perform a method comprising: receiving first image data of a portion of a patient's body at a first image resolution, receiving a plurality of second image data for a plurality of subjects, determining, based on the plurality of second image data, a super resolution model for increasing a resolution of the first image data, and generating, based on the super resolution model and the first image data, third image data of the portion of the patient's body at a second image resolution, wherein the second image resolution is greater than the first image resolution.

Embodiments illustrated under any heading or in any portion of the disclosure may be combined with embodiments illustrated under the same or any other heading or other portion of the disclosure unless otherwise indicated herein or otherwise clearly contradicted by context.

Numerous modifications, alterations, and changes to the described embodiments are possible without departing from the scope of the present invention defined in the claims. It is intended that the present invention not be limited to the described embodiments, but that it has the full scope defined by the language of the following claims, and equivalents thereof.

What is claimed is:

1. A computer-implemented method to generate a three-dimensional model, the computer comprising one or more processors and memory accessible by the one or more processors, the memory storing instructions that when executed by the one or more processors cause the computer to perform the method, the method comprising:
   generating an image modality translation model for converting image data in a second image modality to image data in a first image modality;
   receiving first image data of a first portion of the patient's body in the first image modality;
   receiving second image data of a second portion of the patient's body in the second image modality;
   modifying the second image data from the second image modality to the first image modality by applying the image modality translation model to the second image data; and
   generating, based on the first image data in the first image modality and the modified second image data in the first image modality, a three-dimensional model of the first portion and the second portion of the patient's body.

2. The method of claim 1, wherein generating the image modality translation model comprises:
   receiving a plurality of image data for the first portion of the patient's body in the first image modality for a plurality of subjects; and
   receiving a second plurality of image data for the second portion of the patient's body in the second image modality for the plurality of subjects,
   wherein the image modality translation model is generated based on an analysis of the first plurality of image data and the second plurality of image data.

3. The method of claim 2, wherein the analysis comprises at least one of a Generative Adversarial Network (GAN) analysis, a MedGAN analysis, a super resolution GAN analysis, a pix2pix GAN analysis, a cycleGAN analysis, a discoGAN analysis, a fila-sGAN analysis, a projective adversarial network (PAN) analysis, a variational autoencoders (VAE) analysis, or a regression analysis.

4. The method of claim 1, further comprising determining, based on the three dimensional model of the first portion and the second portion of the patient's body, a transducer array layout map along at least one of the first portion and the second portion of the patient's body.

5. The method of claim 1, wherein the first image modality comprises magnetic resonance imaging (MRI).

6. The method of claim 1, wherein the first portion of the patient's body is a first portion of a body part of the patient and the second portion of the patient's body is a second portion of the body part of the patient.

7. The method of claim 6, wherein the body part is one of a head, a torso, an arm, or a leg.

8. A computer-implemented method to generate a three-dimensional model, the computer comprising one or more processors and memory accessible by the one or more processors, the memory storing instructions that when executed by the one or more processors cause the computer to perform the method, the method comprising:
   receiving first image data of a first portion of a body part of a patient, wherein the first portion of the body part is less than a complete body part;
   receiving a plurality of second image data of the body part for a plurality of subjects;
   generating, based on the plurality of second image data, a body part completion model;
   generating, based on the body part completion model and the first image data, third image data of a second portion of the body part; and
   generating, based on the first image data and the third image data, a three-dimensional model of the body part of the patient.

9. The method of claim 8, further comprising splitting each of the plurality of second image data into a first portion image data and a second portion image data, wherein the first portion image data comprises the first portion of the body part for a corresponding subject and the second portion image data comprises another portion of the body part for the corresponding subject.

10. The method of claim 9, further comprising conducting an analysis of the first portion image data and the second portion image data for each of the plurality of subjects.

11. The method of claim 10, wherein the analysis comprises at least one of a statistical shape analysis, an active appearance analysis, or a global image statistical analysis.

12. The method of claim 8, further comprising determining, based on the first image data, that image data of the second portion of the body part of the patient's body is needed to generate the three-dimensional model of the body part of the patient.

13. The method of claim 8, further comprising determining, based on the three-dimensional model of the body part of the patient, a transducer array layout map along the body part of the patient.

14. The method of claim 8, wherein the three-dimensional model is a complete model of the body part of the patient.

15. The method of claim 8, wherein the body part is a head and wherein the first image data of the first portion of the body part does not include a top portion of the head of the patient.

16. A computer-implemented method to generate a three-dimensional model, the computer comprising one or more processors and memory accessible by the one or more processors, the memory storing instructions that when executed by the one or more processors cause the computer to perform the method, the method comprising:
   receiving first image data of a portion of a patient's body at a first image resolution;
   receiving a plurality of second image data for a plurality of subjects;
   generating, based on the plurality of second image data, a super resolution model for increasing a resolution of the first image data; and
   generating, based on the super resolution model and the first image data, third image data of the portion of the patient's body at a second image resolution, wherein the second image resolution is greater than the first image resolution.

17. The method of claim 16, wherein receiving the plurality of second image data for the plurality of subjects comprises:
   receiving a first plurality of second image data of a same portion of a body as the portion of the patient's body for the plurality of subjects at the first image resolution; and
   receiving a second plurality of second image data of the same portion of the body for the plurality of subjects at the second image resolution,
   wherein generating the super resolution model comprises conducting an analysis of the first plurality of second image data and the second plurality of second image data.

18. The method of claim 17, wherein the analysis comprises at least one of a regression analysis, a convolutional networks analysis, a Generative Adversarial Network (GAN) analysis, a MedGAN analysis, a super resolution GAN analysis, a pix2pix GAN analysis, a cycleGAN analysis, a discoGAN analysis, or a fila-sGAN analysis.

19. The method of claim 17, wherein the first image resolution comprises magnetic resonance imaging.

* * * * *